US008513176B2

(12) United States Patent
Iverson

(10) Patent No.: US 8,513,176 B2
(45) Date of Patent: Aug. 20, 2013

(54) DISINFECTING AND MINERAL DEPOSIT ELIMINATING COMPOSITION AND METHODS

(75) Inventor: Carl E. Iverson, Olympia, WA (US)

(73) Assignee: CH2O Incorporated, Olympia, WA (US)

( * ) Notice: Subject to any disclaimer, the term of this patent is extended or adjusted under 35 U.S.C. 154(b) by 870 days.

(21) Appl. No.: 11/498,495

(22) Filed: Aug. 2, 2006

(65) Prior Publication Data
US 2008/0032905 A1 Feb. 7, 2008

(51) Int. Cl.
C11D 9/34 (2006.01)
C11D 3/395 (2006.01)

(52) U.S. Cl.
USPC ........... 510/247; 510/199; 510/218; 510/219; 510/236; 510/367; 510/379; 510/380; 510/382; 510/436; 510/467

(58) Field of Classification Search
USPC ................. 510/178, 199, 218, 219, 236, 247, 510/367, 379, 380, 382, 436, 467
See application file for complete search history.

(56) References Cited

U.S. PATENT DOCUMENTS

| | | | |
|---|---|---|---|
| 1,488,097 A | 3/1924 | Creger | |
| 2,944,967 A | 7/1960 | Dunklin et al. | |
| 3,149,151 A | 9/1964 | Schiefer et al. | |
| 3,150,081 A | 9/1964 | Haslam et al. | |
| 3,214,454 A | 10/1965 | Blaser et al. | |
| 3,591,515 A | 7/1971 | Lovely | 252/187 |
| 3,702,298 A | 11/1972 | Zsoldos et al. | |
| 3,814,820 A | 6/1974 | Busta et al. | 426/262 |
| 3,869,559 A | 3/1975 | Clark | |
| 3,892,563 A | 7/1975 | La Point | |
| 4,001,443 A | 1/1977 | Dave | 426/106 |
| 4,021,585 A | 5/1977 | Svoboda et al. | 426/332 |
| 4,089,796 A | 5/1978 | Harris et al. | |
| 4,108,772 A | 8/1978 | Alexander | |
| 4,143,115 A | 3/1979 | Ward et al. | 422/113 |
| 4,247,051 A | 1/1981 | Allport | 239/542 |
| 4,261,837 A | 4/1981 | West, Jr. et al. | 210/754 |
| 4,292,292 A | 9/1981 | Hicks et al. | |
| 4,339,468 A | 7/1982 | Kielsmeier | |
| 4,451,444 A | 5/1984 | Santillie et al. | |
| 4,497,713 A | 2/1985 | Geiger | |
| 4,534,866 A | 8/1985 | Becker | |
| 4,534,952 A | 8/1985 | Rapson et al. | |
| 4,568,463 A | 2/1986 | Klein | 210/607 |
| 4,574,084 A * | 3/1986 | Berger | 424/601 |
| 4,590,057 A | 5/1986 | Hicks | |
| 4,610,783 A | 9/1986 | Hudson | |
| 4,618,719 A | 10/1986 | Bay et al. | |
| 4,649,025 A | 3/1987 | Hwa et al. | |
| 4,689,169 A | 8/1987 | Mason et al. | |
| 4,690,772 A | 9/1987 | Tell et al. | 252/106 |
| 4,693,832 A | 9/1987 | Hurst | 210/756 |
| 4,731,193 A | 3/1988 | Mason et al. | |
| 4,759,852 A * | 7/1988 | Trulear | 210/699 |
| 4,802,990 A | 2/1989 | Inskeep, Jr. | |
| 4,850,531 A | 7/1989 | Littleton | 239/1 |
| 4,889,654 A | 12/1989 | Mason et al. | 252/100 |
| 4,913,822 A | 4/1990 | Chen et al. | 210/699 |
| 4,925,645 A | 5/1990 | Mason | |
| 5,009,875 A | 4/1991 | Kelley et al. | |
| 5,047,078 A | 9/1991 | Gill | 71/11 |
| 5,072,022 A | 12/1991 | Bakos et al. | 560/65 |
| 5,084,210 A | 1/1992 | Teeters | 252/392 |
| 5,091,562 A * | 2/1992 | Immenkeppel et al. | 562/24 |
| 5,106,406 A | 4/1992 | Sylling et al. | |
| 5,112,521 A * | 5/1992 | Mullins et al. | 252/180 |
| 5,126,070 A | 6/1992 | Leifheit et al. | 252/186.36 |
| 5,130,052 A | 7/1992 | Kreh et al. | |
| 5,171,477 A | 12/1992 | Kreh | |
| 5,173,258 A | 12/1992 | Childers | 422/27 |
| 5,204,081 A | 4/1993 | Mason et al. | |
| 5,208,031 A | 5/1993 | Kelly | |
| 5,226,972 A | 7/1993 | Bell | 134/25.1 |
| 5,304,236 A | 4/1994 | Fears | |
| 5,314,629 A | 5/1994 | Griese et al. | 210/754 |
| 5,320,779 A | 6/1994 | Fivizzani | |
| 5,324,477 A * | 6/1994 | Schroeder et al. | 422/37 |
| 5,332,580 A | 7/1994 | Young et al. | |

(Continued)

FOREIGN PATENT DOCUMENTS

EP 0 006 065 A2 12/1979
EP 0 017 373 A1 10/1980

(Continued)

OTHER PUBLICATIONS

EPA Guidance Manual, Alternative Disinfectants and Oxidants, Chapter 4. Chlorine Dioxide, pp. 4-1-4-41, Apr. 1999. (41 pages).
International Preliminary Examination Report for International Application No. PCT/US95/02128, mailed May 29, 1997, 6 pages.
International Preliminary Examination Report for International Application No. PCT/US01/24457, mailed Nov. 7, 2002, 5 pages.
International Search Report for International Application No. PCT/US95/02128, mailed Jun. 2, 1995, 2 pages.
International Search Report for International Application No. PCT/US01/24457, mailed Dec. 14, 2001, 1 page.
English Language Internet Translation of JP 8-283112, 6 pages.
English Language Internet Translation of JP 9-71502, 8 pages.
Nowack, "Determination of phosphonates in natural waters by ion-pair high-performance liquid chromatography," *Journal of Chromatography A* 773(1-2):139-146, Jun. 27, 1997. (Abstract).
Nowack et al., "Phosphonate Removal During Water Treatment by Adsorption Onto Activated Sludge and Humic Acids," *Preprints of Extended Abstracts* 40(2):622-624, Symposia Papers Presented Before the Division of Environmental Chemistry, American Chemical Society, Washington, DC, Aug. 20-24, 2000 (5 pages).
Written Opinion for International Application No. PCT/US95/02128, mailed Mar. 14, 1997, 4 pages.

(Continued)

Primary Examiner — Charles Boyer
(74) Attorney, Agent, or Firm — Fish & Richardson P.C.

(57) ABSTRACT

Source water is treated by mixing a first component selected from the group comprising neutralized phosphonic acid compounds, neutralized phosphonate compounds, neutralized derivatives of phosphorus, neutralized anti-scalent polymers, and mixtures thereof, a second component from the group comprising chlorite salt and chlorate salt is admixed to the mixture of the water and the first component, and water. The water and the first and second components are present in amounts sufficient to form a stable liquid composition in which there is substantially no conversion of the second component to chlorine dioxide.

8 Claims, 2 Drawing Sheets

(56) References Cited

U.S. PATENT DOCUMENTS

| | | | |
|---|---|---|---|
| 5,360,550 A | 11/1994 | Clubley et al. | |
| 5,369,099 A | 11/1994 | Iverson, Jr. et al. | |
| 5,389,390 A | 2/1995 | Kross | 426/332 |
| 5,401,419 A | 3/1995 | Kocib | 210/697 |
| 5,405,549 A | 4/1995 | Pitochelli | |
| 5,411,666 A | 5/1995 | Hollis et al. | |
| 5,422,348 A | 6/1995 | Iverson, Jr. et al. | |
| 5,424,032 A | 6/1995 | Christensen et al. | 422/14 |
| 5,451,266 A | 9/1995 | Kirk et al. | 134/25.3 |
| 5,618,440 A | 4/1997 | Mason | |
| 5,799,833 A | 9/1998 | Green et al. | |
| 5,858,443 A | 1/1999 | Hei et al. | |
| 5,863,584 A | 1/1999 | Thomas, Jr. et al. | 426/335 |
| 5,930,950 A | 8/1999 | Iverson, Jr. et al. | 47/58.1 |
| 5,941,635 A | 8/1999 | Stewart | 366/165.5 |
| 6,004,604 A | 12/1999 | Thomas, Jr. et al. | 426/326 |
| 6,017,864 A * | 1/2000 | Brittain et al. | 510/218 |
| 6,036,740 A | 3/2000 | Miller et al. | 71/32 |
| 6,077,480 A | 6/2000 | Edwards et al. | 422/28 |
| 6,083,457 A | 7/2000 | Parkinson et al. | 422/29 |
| 6,096,226 A | 8/2000 | Fuchs et al. | 210/759 |
| 6,120,731 A | 9/2000 | Kross et al. | 422/29 |
| 6,238,573 B1 | 5/2001 | Miller et al. | 210/756 |
| 6,281,278 B1 | 8/2001 | Takase et al. | 524/497 |
| 6,291,411 B1 * | 9/2001 | Callaghan et al. | 510/101 |
| 6,325,970 B1 | 12/2001 | Parkinson et al. | 422/29 |
| 6,345,632 B1 | 2/2002 | Ludwig et al. | 134/22.11 |
| 6,350,410 B1 | 2/2002 | Iverson et al. | 422/29 |
| 6,362,152 B1 | 3/2002 | Young et al. | |
| 6,428,696 B2 * | 8/2002 | Kuke | 210/192 |
| 6,767,470 B2 | 7/2004 | Iverson et al. | 210/699 |
| 6,840,251 B2 * | 1/2005 | Gill et al. | 134/22.12 |
| 6,852,348 B2 | 2/2005 | Iverson et al. | |
| 6,881,320 B1 | 4/2005 | Krafton et al. | 205/556 |
| 7,033,510 B2 | 4/2006 | Cilliers et al. | 210/754 |
| 7,186,376 B2 | 3/2007 | Iverson et al. | 422/37 |
| 7,252,769 B2 | 8/2007 | Dickinson | 210/699 |
| 7,266,924 B2 | 9/2007 | Van De Lande | 47/62 R |
| 7,601,266 B2 | 10/2009 | Iverson | 210/696 |
| 2001/0009897 A1 * | 7/2001 | Bauer et al. | 510/511 |
| 2002/0014463 A1 * | 2/2002 | Iverson et al. | 210/749 |
| 2002/0061236 A1 | 5/2002 | Inoue | |
| 2002/0061263 A1 | 5/2002 | Taylor | 422/129 |
| 2003/0139310 A1 * | 7/2003 | Smith et al. | 510/278 |
| 2003/0200997 A1 | 10/2003 | Gill et al. | 134/22.12 |
| 2003/0216271 A1 * | 11/2003 | Scheper et al. | 510/220 |
| 2005/0075263 A1 * | 4/2005 | Gomez | 510/375 |
| 2005/0217176 A1 | 10/2005 | Van De Lande | 47/62 N |
| 2006/0054563 A1 * | 3/2006 | Tsuneki et al. | 210/697 |
| 2006/0089285 A1 * | 4/2006 | Ahmed et al. | 510/370 |
| 2006/0153766 A1 | 7/2006 | Iverson et al. | 423/472 |
| 2007/0117215 A1 | 5/2007 | Davis et al. | |
| 2008/0032905 A1 | 2/2008 | Iverson | |
| 2008/0258104 A1 * | 10/2008 | Mullins et al. | 252/187.28 |
| 2009/0294381 A1 * | 12/2009 | Coffey et al. | 210/753 |
| 2009/0298689 A1 | 12/2009 | Iverson | 504/116.1 |
| 2010/0086514 A1 * | 4/2010 | Liu et al. | 424/78.08 |

FOREIGN PATENT DOCUMENTS

| | | |
|---|---|---|
| EP | 0 225 051 A1 | 6/1987 |
| EP | 0 251 955 A1 | 1/1988 |
| EP | 0 380 171 A1 | 8/1990 |
| ES | 2 043 238 | 12/1993 |
| ES | 2 315 167 B2 | 3/2009 |
| GB | 746615 | 3/1956 |
| HU | 38594 A | 6/1986 |
| JP | 5-57287 A | 3/1993 |
| JP | 8-283112 | 10/1996 |
| JP | 9-71502 | 3/1997 |
| JP | 11-130407 A | 5/1999 |
| MX | 2007000550 A | 2/2009 |
| PL | 154449 B1 | 7/1989 |
| WO | 95/23510 A1 | 9/1995 |
| WO | WO 96/25049 A1 | 8/1996 |
| WO | WO 96/32523 A1 | 10/1996 |
| WO | 97/33477 A1 | 9/1997 |
| WO | 98/00012 A1 | 1/1998 |
| WO | 00/48470 A1 | 8/2000 |
| WO | WO 01/58265 A2 | 8/2001 |
| WO | WO 02/12130 A1 | 2/2002 |

OTHER PUBLICATIONS

Written Opinion for International Application No. PCT/US01/24457, mailed Jul. 12, 2002, 4 pages.
3 Sheets from Unocal Agriproducts Advertising, Unocal 76, P.O. Box 60455, Los Angeles, CA 90060, 1992 & 1994.
"Broadening the Scope of Chlorine Dioxide Technology" (brochure), Rio Linda Chemical Co., Inc.
"Chlorine Dioxide: An Alternative to Chlorine?," *Packer Shipper*, Jun. 1996, 4pgs.
"Chlorine Dioxide Use in Fruit and Vegetable Processing" (brochure), Rio Linda Chemical Co., Inc.
"Pride Packaging Co. Tries Chlorine Dioxide," *Hort Expo Northwest*, Dec. 1995, 3 pgs.
Bernarde, M. et al., "Efficiency of Chlorine Dioxide as a Bactericide," Applied Microbiology, Sep. 1965, vol. 13, No. 5 and pp. 776-780.
Carrillo, A. et al., "Application of Diluted Chlorine Dioxide to Radish and Lettuce Nursuries Insignificantly Reduced Plant Development," Ecotoxicology and Environmental Safety, 1996, vol. 35 at pp. 57-66.
Chastagner et al., "Potential Use of Chlorine Dioxide to Control Diseases in Ornamental Plant Production Systems," Plant Propagators' Society, Sep. 10, 2002, vol. 51 at pp. 275-279.
Chem Fresh, Inc., Oxicide (brochure).
Chlorine Dioxide Disinfection of Produce Washwater, AEIS 653, www.msu.edu/~brook/publications/aeis/aeis653.htm, Jul. 1998. Downloaded Sep. 16, 2011.
Chlorine Dioxide Disinfection of Produce Washwater, AEIS 654, www.msu.edu/~brook/publications/aeis/aeis654.htm, Jul. 1998. Downloaded Sep. 16, 2011.
Guideline No. 15, "Microbiological Control of Food Industry Process Waters: Guidelines on the Use of Chlorine Dioxide and Bromine as Alternatives to Chlorine," Campden & Chorleywood Food Research Association, Jul. 1997. 62 pages.
Gurol, M., "Facts and Myths about Irrigation Water," www.eco-web.com/edi/051201.html, Dec. 2005. Downloaded Sep. 30, 2011.
International Dioxide, Inc., Chlorine Dioxide (brochure).
Irrigation Journal, May/Jun. 1987 "Conditionerigation: New Process Proves Successful," pp. 12-15.
New Jersey Dept. of Health and Senior Services, Hazardous Substance Fact Sheet, "Chlorine Dioxide," Jun. 1998, rev. Dec. 2005.
Roberts, R., "Integrating Biological Control into Postharvest Disease Management Strategies," HortScience, Jul. 1994, vol. 29, No. 7 at pp. 758-762.
Selectrocide 12G Product Packaging, Rev 5-05A.
Simpson, G., "Biofilm: Removal and Prevention with Chlorine Dioxide," An International Symposium on Chlorine Dioxide: Process Water, Drinking Water and Water Waste Issues, Sep. 14-15, 1995, New Orleans, LA.
Simpson, G. et al., "A Focus on Chlorine Dioxide: The 'Ideal' Biocide," Unichem International, Inc., Houston, Texas, Jul. 1993.
Spotts, R.A., "Chlorine and Chlorine Dioxide for Control of d'Anjou Pear Decay," Plant Disease, Dec. 1980, vol. 64, No. 12 at pp. 1095-1097.
Steel, "Water Supply and Sewerage," 3rd Ed. pp. 421-437, McGraw-Hill Book Co., Inc. 1953.
Iverson et al., "Method of Promoting Unrestricted Flow of Irrigation Water Through Irrigation Networks," Office Action in Ex Parte Reexamination, for Reexamination Control No. 90/011,958, mailed Aug. 17, 2012, 31 pages.
Iverson et al., "Method of Promoting Unrestricted Flow of Irrigation Water Through Irrigation Networks," Office Action in Ex Parte Reexamination, for Reexamination Control No. 90/011,958, mailed Mar. 15, 2012, 18 pages.
Iverson et al., "Method of Promoting Unrestricted Flow of Irrigation Water Through Irrigation Networks," Patent Owner's Response Under 37 CFR 1.111, for Reexamination Control No. 90/011,958, mailed May 15, 2012, 38 pages.

* cited by examiner

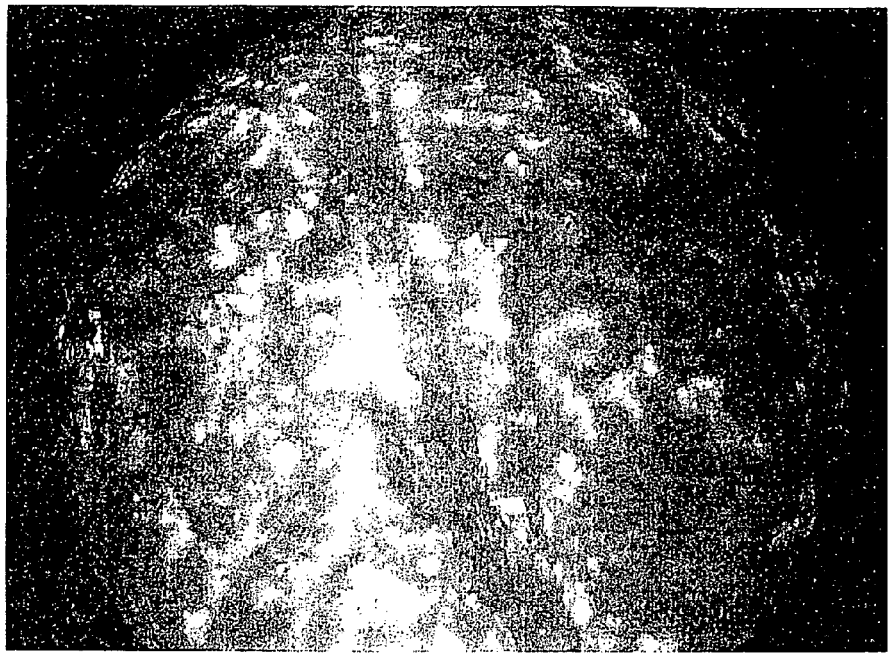
BLANK: 40X1
TREATED: 40X-1

DISINFECTING AND MINERAL DEPOSIT ELIMINATING COMPOSITION AND METHODS

TECHNICAL FIELD

This invention relates to a composition for disinfecting source water and surfaces contacted by the source water, and for substantially eliminating mineral deposits on surfaces. More particularly, it relates to a stable disinfecting/mineral treating composition in water that does not produce dangerous gaseous compounds when mixed with the water.

BACKGROUND OF THE INVENTION

Municipal water, surface water and well water contain varying amounts of pathogens, dissolved oxygen and minerals. The pathogens form biofilms that cause disease and corrosion. Dissolved minerals in the water form crystalline structures that restrict passageways and reduce water flow. There is a need for providing a low cost composition that will effectively eliminate microorganisms and prevent crystalline mineral deposits and that only requires a simple feed of the composition from a container into the source water via an inexpensive metering pump. It is an object of the invention to fill this need.

It is an object of the present invention to reduce or eliminate microorganisms and also prevent crystalline mineral deposits and to do so without generating substantial amounts of chlorine dioxide and/or creating risk of dangerous exothermic and explosive reactions.

Another object of the present invention is to produce an effective composition for reducing or eliminating microorganisms and crystalline mineral deposits without the need for expensive equipment and/or the monitoring and testing of the equipment to assure safe operation.

BRIEF SUMMARY OF THE INVENTION

The composition of the present invention is a disinfectant mineral treatment that causes mineral deposits to become amorphous. The composition is formed by admixing two components in the presence of water. One component is selected from the group consisting of neutralized phosphonate compounds, neutralized phosphonic acid compounds, neutralized derivatives of phosphorus, blends of neutralized phosphonate compounds, neutralized phosphonic acid compounds and neutralized phosphorus derivatives, neutralized anti-scalent polymers, and mixtures thereof. The neutralized phosphonate may be selected from the group consisting of, but not limited to; aminotri(methylene phosphonic Acid) (ATMP), 1-hydroxyethylidene-1,1-diphosphonic acid (HEDP), ethylenediaminetetra (methylene phosphonic acid) (EDTMPA), hexamethylenediaminetetra(methylene phosphonic acid) (HMDTMPA), diethylenetriaminepenta(methylene phosphonic acid) (DETPMPA), bis(hexamethylenetriamine penta(methylene phosphonic acid)) (BHMPTMPA), 2-phosphonobutane1,2,4-tricarboxylic acid (PBTC), 2-hydroxy phosphonoacetic acid (HPA), phosphinocarboxylic acid (PCA), nitrilotris(methylene phosphonic acid) (NTMP), and diethylenetriaminepenta(methylene phosphonic acid) (DTMP). A preferred neutralized phosphonate is 2 phosphonobutane-1,2,4-tricarboxylic acid (PBTC), and mixtures thereof.

The first component is neutralized to a pH of at least about 7.0 before or after it is admixed with water. Then, a second component, selected from the group comprising chlorite salt and chlorate salt, is admixed to the mixture of the first component and water. The water and the first and second components are present in amounts sufficient to form a stable liquid composition in which there is substantially no conversion of the second component (the salt component) to chlorine dioxide.

After it is made, the composition is stored in containers until used. When used, the composition is pumped out from the container, into source water, using an inexpensive metering pump.

The composition of this invention has a pH of 7.0 or higher. The second component is preferably about a 1% to about a 25% solution of sodium chlorite in water.

A method of the invention involves the use of the composition for converting minerals in the source water to amorphous mineral deposits on surfaces contacted by the source water. The amorphous deposits are easily removed from the surfaces, such as by wiping and/or washing.

Another method of the invention comprises disinfecting source water and surfaces by use of the same two component composition.

These and other advantages and features will become apparent from the detailed description of the best mode for carrying out the invention that follows.

BRIEF DESCRIPTION OF THE DRAWING

FIG. 2 is a photograph of the "blank" sample taken under a microscope at 40×-1; and FIG. 3 is a photograph of the "treated" sample under the microscope, also at 40×-1.

DETAILED DESCRIPTION OF THE PREFERRED EMBODIMENT

Figure 1:
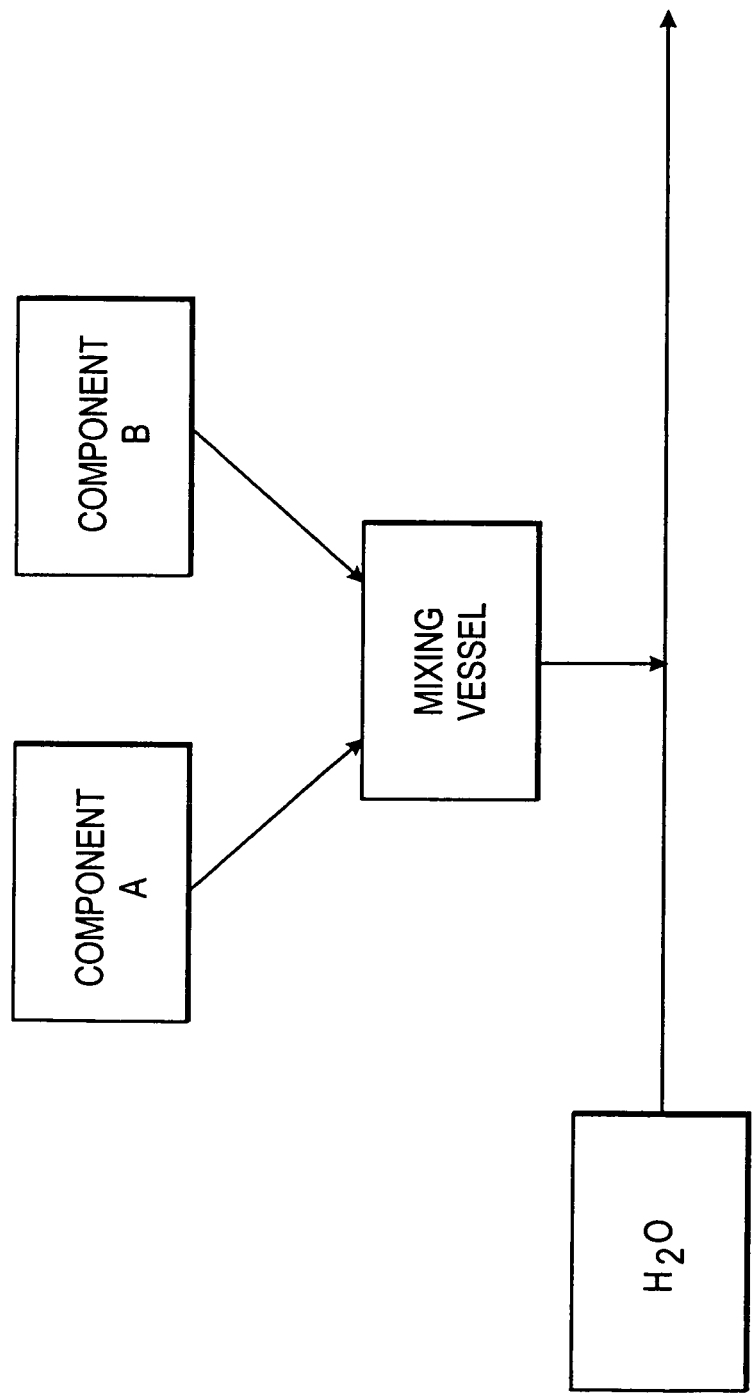
FIG. 1 is a flow diagram a water conduit flowing from a source of water, showing a component A being added to the water in the conduit and showing component B being added to the mixture of the water and the component A.

Referring to FIG. 1, a component A and a component B are shown to be mixed together in a mixing vessel. The mixture is then admixed to source water flowing through a conduit 10. Component A is selected from the group consisting of neutralized phosphonate compounds, neutralized phosphonic acid compounds, neutralized derivatives of phosphorus, blends of neutralized phosphonate compounds, neutralized phosphonic acid compounds and neutralized phosphorus derivatives, neutralized anti-scalent polymers, and mixtures thereof. The neutralized phosphonate may be selected from the group consisting of, but not limited to; ATMP, HEDP, EDTMPA, HMDTMPA, DETPMPA, PHMPTMPA, PBTC, HPA, PCA, NTMP, AND DTPMP. A preferred neutralized phosphonate is 2 phosphonobutane-1, 2, 4-tricarboxylic acid (PBTC). Component B is selected from the group comprising chlorite salt and chlorate salt.

One or more of the component A substances may be added to water in a container. The component A is admixed with the water. Component A can be acquired in a dry granular form or in a liquid form. It is important that the mixture of the component A and the water have a pH 7.0 or higher before it and the component B are combined. Component B is a salt and it can be acquired in a dry granular form or in a liquid form. The essential thing is that component A be neutralized so that its pH is at least 7.0 so that when component B the salt compound is added. In the presence of water, the two components A and B and the water will form a stable liquid composition in which there is substantially no conversion of the second component, viz. the chlorite salt or the chlorate salt, to chlorine dioxide.

Another way or preparing the composition is to mix component A with component B and then admix the mixture with water.

Referring to FIG. 1, a component A and a component B are shown to be mixed together in a mixing vessel. The mixture is then admixed to source water flowing through the conduit 10. Component A is selected from the group consisting of neutralized phosphonate compounds, neutralized phosphonic acid compounds, neutralized derivatives of phosphorus, blends of neutralized phosphonate compounds, neutralized phosphonic acid compounds and neutralized phosphorus derivatives, neutralized anti-scalent polymers, and mixtures thereof. The neutralized phosphonate may be selected from the group consisting of, but not limited to; aminotri(methylene phosphonic Acid) (ATMP), 1-hydroxyethylidene-1,1-diphosphonic acid (HEDP), ethylenediaminetetra (methylene phosphonic acid) (EDTMPA), hexamethylenediaminetetra(methylene phosphonic acid) (HMDTMPA), diethylenetriaminepenta(methylene phosphonic acid) (DETPMPA), bis(hexamethylenetriamine penta (methylene phosphonic acid)) (BHMPTMPA), 2-phosphonobutane-1,2,4-tricarboxylic acid (PBTC), 2-hydroxy phosphonoacetic acid (HPA), phosphinocarboxylic acid (PCA), nitrilotris(methylene phosphonic acid) (NTMP), and diethylenetriaminepenta(methylene phosphonic acid) (DTMP). A preferred neutralized phosphonate is 2 phosphonobutane-1,2,4-tricarboxylic acid (PBTC). Component B is selected from the group comprising chlorite salt and chlorate salt.

EXAMPLE #1

Neutralized Phosphonate/Sodium Chlorite Experiment

Collect a sample of pond water or equivalent that is known to contain biological life. Reserve some of the contaminated water to use as a "blank". Add one part neutralized phosphonate chlorite solution to yield 5 ppm NaClo2 and 5.9 ppm PBTC. Tests confirmed residuals. Allow the treated water to sit for approximately 10 minutes before proceeding. Test the blank solution and the treated solution with BTM-2 biological kit and fungi plate; note biological growth over time. On Day 3, the Blank was observed with approximately 10 distinct colonies of bacterial growth; moderate pink on about ½ of agar. There was a lot of mold growth. On Day 3 the treated growth media had no bacterial and no yeast/mold growth.

EXAMPLE #2

Neutralized Phosphonate/Sodium Chlorite Experiment

Collected two liters of tap water. Calcium chloride and sodium carbonate were added to each liter yielding solutions with approximately 250 ppm hardness. One of the liters was used as a "blank". The other liter was treated with neutralized phosponate/sodium chlorite solution to yield 5.0 NaClO2 and 5.9 ppm PBTC. Heated the solutions for 10 hours, insuring the water volume did not evaporate below 100 mls.

Remove 1.0 ml of the treated, heated and condensed water and place it on a microscope slide. Allow the sample to dry naturally in the atmosphere. FIG. 2 is a photo of the "blank" sample under the microscope at 40×-1. FIG. 3 is a photo of the "treated" sample under the microscope at 40×-1.

Observations of Dried Blank: This made thick white film on the slide. There are white crystals with "knobs" visible to the naked eye. Under the scope, crystals are dark and rough looking with large dark knobs. The edge of the film had more "snowflake' shaped crystals with knobs.

Observation of Dried sample treated with neutralized phosphonate/sodium chlorite product: This made a thin opaque white film, crystals were long, sparse & thin and they were not agglomerated into a dense structure as the blank was.

The conclusion: under identical circumstances, the treated solution had substantially less crystalline substance than the blank solution.

EXAMPLE #3

Neutralized Phosphonate/Sodium Chlorite Experiment

Collect four liters of tap water. Calcium chloride and sodium carbonate were added to two liters, yielding solutions with approximately 250 ppm hardness. Treat one of the plain tap water and one of the hard water liters with neutralized phosphonate/sodium chlorite solution to yield 5.0 ppm NaClo2 and 5.9 ppm PBTC. Cleanly cut (at an angle) the bottom of 16 fresh rose stems; place four stems into each beaker and observe results over 8 days.

Conclusion

From the information included, we can see the roses treated with neutralized phosphonate/sodium chlorite solution (5.0 NaClO2 and 5.9 ppm PBTC) demonstrated the longest shelf-life. This was particularly visible in hard water since biofilm and hardness mineral crystallization can accumulate in the stems, inhibiting the uptake of water.

| | TAP WATER | |
|---|---|---|
| | Tap-BLANK | Tap-Treated |
| Day 1: Apr. 14, 2006 | 2 yellow, 2 pink; all buds | 2 yellow, 2 pink; all buds |
| Day 2 | Saturday, no observations | Saturday, no observations |
| Day 3 | Sunday, no observations | Sunday, no observations |
| Day 4 | All buds open. 2 pinks w/brown on petals; 1 pink w/dried leaves. | All buds opening & healthy. All leaves green. |
| Day 5 | Same as day 4. | Sane as day 4 |
| Day 6 | Same as day 4 | Same as day 4 |
| Day 7 | Same as day 4. Both pinks mostly brown, 1 pink dying. | Same as day 4 |
| Day 8 | 2 yellow are healthy; 2 pink dead. | 3 open & healhy; 1 pink wilting with dried leaves |

| | HARD WATER | |
|---|---|---|
| | Hard-BLANK | Hard-Treated |
| Day 1; Apr. 14, 2006 | 2 pink, 2 yellow. All buds. | 2 pink, 2 yellow. All buds. |
| Day 2 | Saturday, no observations. | Saturday, no observations. |
| Day 3 | Sunday, no observations. | Sunday, no observations. |

-continued

| | HARD WATER | |
|---|---|---|
| | Hard-BLANK | Hard-Treated |
| Day 4 | All open & healthy. 1 yellow has minor blemishes. | All open & healthy. |
| Day 5 | Same as day 4 | Same as day 4 |
| Day 6 | All 4 open & healthy, leaves starting to dry out. | Same as day 4 |
| Day 7 | 1 healthy, 1 wilting yellow. 2 healthy pink. All leaves dried. | Same as day 4, leaves just starting to dry a little. |
| Day 8 | 1 yellow healthy w/dry leaves 3 dying w/dried leaves. | All open & healthy, minor leaf drying. |

Observations:

| TRIAL # | TREATED, TAP WATER | TREATED, HARD WATER | AVERAGE |
|---|---|---|---|
| BLANK | * | * | worst |
| TREATED | ***** | ***** | best |

* = WORST
***** = BEST

What is claimed is:

1. A water conduit treating composition comprising a pH of 7.0 or higher and consisting essentially of a first component, a second component and water, wherein the water conduit treating composition is prepared by a process comprising:
   mixing the first component, the second component, and water such that the first and second components are present in amounts sufficient to form a stable liquid composition having a pH of 7.0 or higher,
   wherein:
      the first component is neutralized 2-phosphonobutane-1,2,4-tricarboxylic acid (PBTC),
      the second component is selected from $ClO_2^-$ salts and $ClO_3^-$ salts, and
      the water conduit treating composition does not harm plants when added to a source water.

2. The water conduit treating composition of claim 1, wherein the second component is a $ClO_2^-$ salt.

3. The water conduit treating composition of claim 2, wherein the second component is $NaClO_2$.

4. The water conduit treating composition of claim 3, wherein the second component is an aqueous solution of $NaClO_2$ with a concentration of about 1% to about 25%.

5. A water conduit treating composition comprising a pH of 7.0 or higher and consisting essentially of a first component, a second component, and water, wherein the water conduit treating composition is prepared by a process comprising:
   mixing the first component, the second component, and water such that the first and second components are present in amounts sufficient to form a stable liquid composition having a pH of 7.0 or higher,
   wherein:
      the first component is neutralized 2-phosphonobutane-1,2,4-tricarboxylic acid (PBTC), and
      the second component is selected from $ClO_2^-$ salts and $ClO_3^-$ salts.

6. The water conduit treating composition of claim 5, wherein the second component is a $ClO_2^-$ salt.

7. The water conduit treating composition of claim 6, wherein the second component is $NaClO_2$.

8. The water conduit treating composition of claim 7, wherein the second component is an aqueous solution of $NaClO_2$ with a concentration of about 1% to about 25%.

* * * * *